United States Patent
Baiera et al.

(10) Patent No.: US 9,996,543 B2
(45) Date of Patent: Jun. 12, 2018

(54) COMPRESSION AND OPTIMIZATION OF A SPECIFIED SCHEMA THAT PERFORMS ANALYTICS ON DATA WITHIN DATA SYSTEMS

(71) Applicant: International Business Machines Corporation, Armonk, NY (US)

(72) Inventors: James C. Baiera, Medina, OH (US); Jill R. Doty, Cleveland, OH (US)

(73) Assignee: International Business Machines Corporation, Armonk, NY (US)

( * ) Notice: Subject to any disclaimer, the term of this patent is extended or adjusted under 35 U.S.C. 154(b) by 318 days.

(21) Appl. No.: 14/989,008

(22) Filed: Jan. 6, 2016

(65) Prior Publication Data
US 2017/0192999 A1    Jul. 6, 2017

(51) Int. Cl.
G06F 17/30    (2006.01)

(52) U.S. Cl.
CPC .. G06F 17/30153 (2013.01); G06F 17/30156 (2013.01); G06F 17/30911 (2013.01); G16H 10/60 (2018.01)

(58) Field of Classification Search
CPC ......... G06F 17/30153; G06F 17/30156; G06F 19/322
USPC ...................................................... 707/692
See application file for complete search history.

(56) References Cited

U.S. PATENT DOCUMENTS

| 5,690,893 A | * | 11/1997 | Ozawa | ............ | C01N 35/00732 |
| | | | | | 422/63 |
| 6,499,023 B1 | * | 12/2002 | Dong | ................... | G06Q 30/02 |
| | | | | | 706/46 |
| 7,810,085 B2 | * | 10/2010 | Shinnar | .................. | G06F 8/443 |
| | | | | | 717/156 |

(Continued)

FOREIGN PATENT DOCUMENTS

| EP | 000752648 A1 | 1/1997 |
| WO | 0016250 A1 | 3/2000 |
| WO | 2005122022 A3 | 3/2006 |

OTHER PUBLICATIONS

Groppe et al., "Satisfiability-Test, Rewriting and Refinement of Users' XPath Queries According to XML Schema Definitions", ADBIS 2006, LNCS 4152, pp. 22-38, 2006. (Year: 2006).*

(Continued)

*Primary Examiner* — Phuong Thao Cao
(74) *Attorney, Agent, or Firm* — Ingrid M. Foerster; Edell, Shaprio & Finnan, LLC

(57) ABSTRACT

A system optimizes performance of analytics and includes at least one processor. The system analyzes a specification of an analytic produced in accordance with a schema, where the specification indicates a set of conditions for members of a population to determine the analytic. The system compresses the specification by modifying constructs within the specification to produce a compressed specification of a reduced size and complying with the schema, where modifying the constructs within the specification includes removing duplicate portions, combining logical conditions, and (Continued)

removing portions with unused data. The system further performs the analytic based on the compressed specification. Embodiments further include a method and computer program product for optimizing performance of analytics in substantially the same manner as the system.

20 Claims, 7 Drawing Sheets

(56) References Cited

U.S. PATENT DOCUMENTS

| | | | | |
|---|---|---|---|---|
| 8,266,606 | B2* | 9/2012 | Dickenson | G06F 9/5016 |
| | | | | 711/170 |
| 8,539,440 | B1* | 9/2013 | Liang | G06F 8/34 |
| | | | | 715/763 |
| 9,075,869 | B1* | 7/2015 | Osband | G06F 17/30684 |
| 9,589,019 | B2* | 3/2017 | Clifford | G06F 17/30469 |
| 9,680,897 | B2* | 6/2017 | Tully | H04L 65/602 |
| 2002/0099701 | A1* | 7/2002 | Rippich | G06F 17/30967 |
| 2005/0100232 | A1 | 5/2005 | Sakanash et al. | |
| 2005/0246306 | A1 | 11/2005 | Evans et al. | |
| 2006/0048107 | A1* | 3/2006 | Thiagarajan | G06F 8/10 |
| | | | | 717/136 |
| 2007/0038651 | A1* | 2/2007 | Bernstein | G06F 17/30587 |
| 2007/0186211 | A1* | 8/2007 | Crasovan | G06F 8/41 |
| | | | | 717/140 |
| 2008/0104579 | A1* | 5/2008 | Hartmann | G06F 17/2247 |
| | | | | 717/136 |
| 2011/0145286 | A1* | 6/2011 | LaRowe | G06F 17/30864 |
| | | | | 707/780 |
| 2011/0295892 | A1 | 12/2011 | Evans et al. | |
| 2012/0331120 | A1* | 12/2012 | Daute | G06F 8/71 |
| | | | | 709/223 |
| 2013/0246997 | A1* | 9/2013 | Liang | G05B 19/0426 |
| | | | | 717/105 |
| 2014/0032240 | A1 | 1/2014 | Lougheed et al. | |
| 2014/0149366 | A1* | 5/2014 | Huang | G06F 17/30156 |
| | | | | 707/692 |
| 2014/0188900 | A1* | 7/2014 | Sankaran | H03M 7/3097 |
| | | | | 707/749 |
| 2014/0201126 | A1 | 7/2014 | Zadeh et al. | |
| 2014/0278525 | A1* | 9/2014 | Curran | G06F 19/322 |
| | | | | 705/3 |
| 2015/0006667 | A1 | 1/2015 | Foerster et al. | |
| 2015/0039326 | A1* | 2/2015 | Cutshall | G06Q 50/22 |
| | | | | 705/2 |
| 2015/0331895 | A1* | 11/2015 | Zhang | B60N 2/5685 |
| | | | | 707/690 |
| 2016/0162825 | A1* | 6/2016 | Dan | G06Q 10/06375 |
| | | | | 705/7.37 |
| 2017/0039241 | A1* | 2/2017 | Bhagwan | G06F 17/30463 |
| 2017/0046311 | A1* | 2/2017 | Walker | G06F 17/211 |
| 2017/0192999 | A1* | 7/2017 | Baiera | G06F 17/30153 |

OTHER PUBLICATIONS

"The Explorys Platform", IBM Watson Health, Solution Brief, Produced in the United States of America, Nov. 2015, 4 pages.

Krishnan et al.; "A universal parallel two-pass MDL context tree compression algorithm." (2014). IEEE Journal of Selected Topics in Signal Processing, vol. 9, No. 4, Jun. 2015, pp. 741-748.

* cited by examiner

COMPRESSION AND OPTIMIZATION OF A SPECIFIED SCHEMA THAT PERFORMS ANALYTICS ON DATA WITHIN DATA SYSTEMS

BACKGROUND

1. Technical Field

Present invention embodiments relate to performing analytics on data stored within data systems, and more specifically, to optimizing performance of analytics by compression of patient centric or patient defined measures within a specified schema that performs such data analytics.

2. Discussion of the Related Art

Healthcare networks have very complicated organization structures. An organization typically comprises multiple source systems (e.g., a source of electronic medical records including electronic health records (EHR), records from a claims system, lab feed, various data sources implementing the HL7 standard, patient satisfaction survey, etc.). Clinically integrated networks (CIN) or galaxies (e.g., a group of organizations) are collections of individual healthcare systems with data sharing agreements. Analytics are applied to various electronic records within the source systems to obtain relevant data based upon queries by end users. Data analytics can be performed within the source systems to determine measures for particular patient populations, where the measures are defined by specifications within a schema used to analyze the data (e.g., an XML type language). However, due to the nature of human defined documents, duplicate codes and/or extraneous codes as well as other types of codes within the measure defined specifications may result in inefficiencies in processing of such specifications.

SUMMARY

According to one embodiment of the present invention, a system optimizes performance of analytics and includes at least one processor. The system analyzes a specification of an analytic produced in accordance with a schema, where the specification indicates a set of conditions for members of a population to determine the analytic. The system compresses the specification by modifying constructs within the specification to produce a compressed specification of a lesser or reduced size and complying with the schema, where modifying the constructs within the specification includes removing duplicate portions, combining logical conditions, and removing portions with unused data. The system further performs the analytic based on the compressed specification.

Embodiments of the present invention further include a method and computer program product for optimizing performance of analytics in substantially the same manner described above.

BRIEF DESCRIPTION OF THE DRAWINGS

Generally, like reference numerals in the various figures are utilized to designate like components.

DETAILED DESCRIPTION

Figure 1:
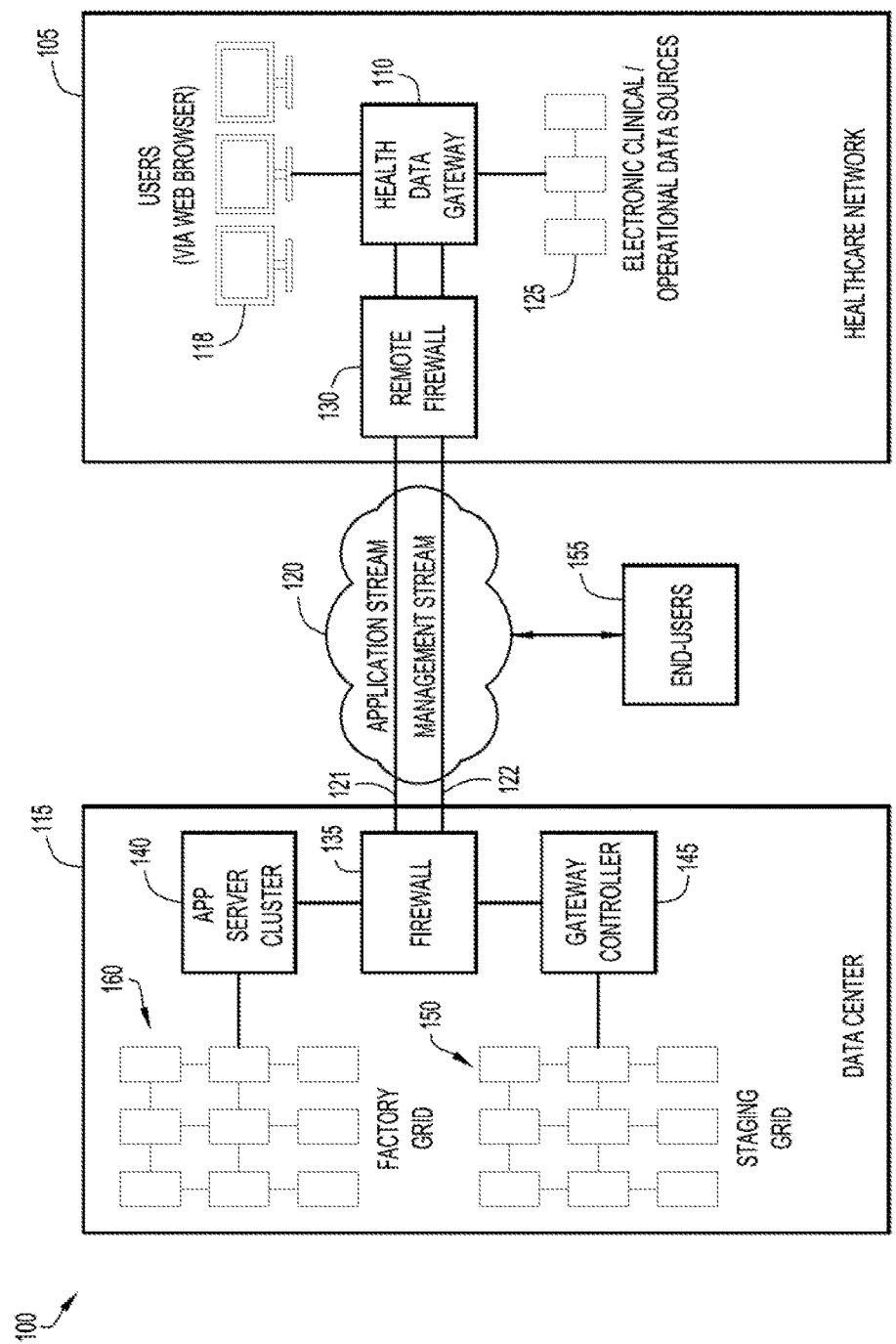
FIG. 1 is a diagrammatic illustration of an example computing environment according to an embodiment of the present invention.

An organization may comprise multiple source systems (e.g., a source of electronic medical records including electronic health records (EHR), records from a claims system, lab feed, various data sources implementing the HL7 standard, patient satisfaction survey, etc.), while clinically integrated networks (CIN) or galaxies (e.g., a group of organizations) are collections of individual healthcare systems with data sharing agreements. These agreements may define restrictions on how the data may be used, and such restrictions must be complied with according to an entity's data governance policies and procedures.

Present invention embodiments pertain to performing analytics on data within the multiple source systems of the organization. The analytics performed on the data are based upon patient centric measures (also referred to herein as patient defined measures) that are defined, e.g., by a clinical team of professionals based upon established guidelines and specifications associated with specific types of medical issues associated with a patient population. In particular, one or more human defined measures are provided to define a desired patient population for performing analytics on the data, where a patient defined measure is defined by a specification (also referred to herein as a measure definition) for performing analytics that is in accordance with a particular schema (e.g., an XML schema) and that further indicates a set of conditions for members of a population (e.g., patient conditions). The specification or measure definition that defines the measure can includes statements or lines of the specification that provide criteria and/or logical conditions (e.g., OR statements, AND statements, etc.) that are analyzed by analytic engines. The analytic engines of the invention embodiments include a measure engine and an optimizer provided within a data center. The measure engine determines one or more measure specifications defining one or more patient populations. The optimizer analyzes and compresses each measure specification as necessary by modifying constructs within the specification to produce a compressed specification of a lesser or reduced size while still complying with the schema. The modification of constructs within the specification by the measure engine includes removing duplicate portions, combining logical conditions, and removing portions with unused data. An analytic is then performed based upon or utilizing the compressed specification. The analytic is performed, e.g., on patient healthcare records within the source systems to obtain patient information based upon the measure definition (e.g., number of patients associated with one or more groups or medical conditions, ratios of patients in smaller groups or conditions in relation to larger groups or conditions, etc.).

Present invention embodiments provide several advantages. For example, compression of the measure defined specification provides a smaller memory footprint and enables more efficient processing of data analytics by other analytic engines downstream from the optimizer (e.g. optimizing parallel processing of data). This in turn increases throughput of data for its end usage.

An example computing environment for use with present invention embodiments is illustrated in FIG. 1. Computing environment 100 includes a healthcare network 105 in communication with a data center 115 over a communications network 120 (e.g., providing a secure virtual private network (VPN)). The communications over network 120 preferably occur between a firewall 130 of healthcare network 105 and a firewall 135 of data center 115. The communications over network 120 may include an application stream 121 pertaining to communications for applications and a management stream 122 pertaining to communications for managing the data. The network may be implemented by any number of any suitable communications media (e.g., wide area network (WAN), local area network (LAN), Internet, Intranet, etc.). Alternatively, healthcare network 105 and data center 115 may be local to each other, and communicate via any appropriate local communication medium (e.g., local area network (LAN), hardwire, wireless link, Intranet, etc.).

Healthcare network 105 includes a health data gateway 110 coupled to end-user systems 118 and one or more clinical/operational data sources 125 providing various medical information (e.g., electronic health records (EHR), records from a claims system, lab feed, various data sources implementing the HL7 standard, patient satisfaction survey, etc.) stored according to a source data model.

Data center 115 includes an application server cluster 140, a gateway controller 145, a staging grid 150, and a factory grid 160. Health data gateway 110 of healthcare network 105 is configured to acquire data from data sources 125 and transmit the acquired data to gateway controller 145 of data center 115. The gateway controller receives the incoming data from the communications network and processes that data to staging grid 150. The staging and factory grids each include a cluster of computer systems to store data and perform parallel processing. By way of example, the staging and factory grids each employ a HADOOP cluster with a HADOOP distributed file system (HDFS).

Staging grid 150 inspects and publishes the data to factory grid 160 in accordance with a data model employed by the factory grid. Factory grid 160 includes various engines to perform desired analytics on the data based on queries received from end-user systems 118 and other end-user systems 155 accessing data center 115 over network 120. The queries are handled in conjunction with application server cluster 140 to produce desired results.

Figure 2:
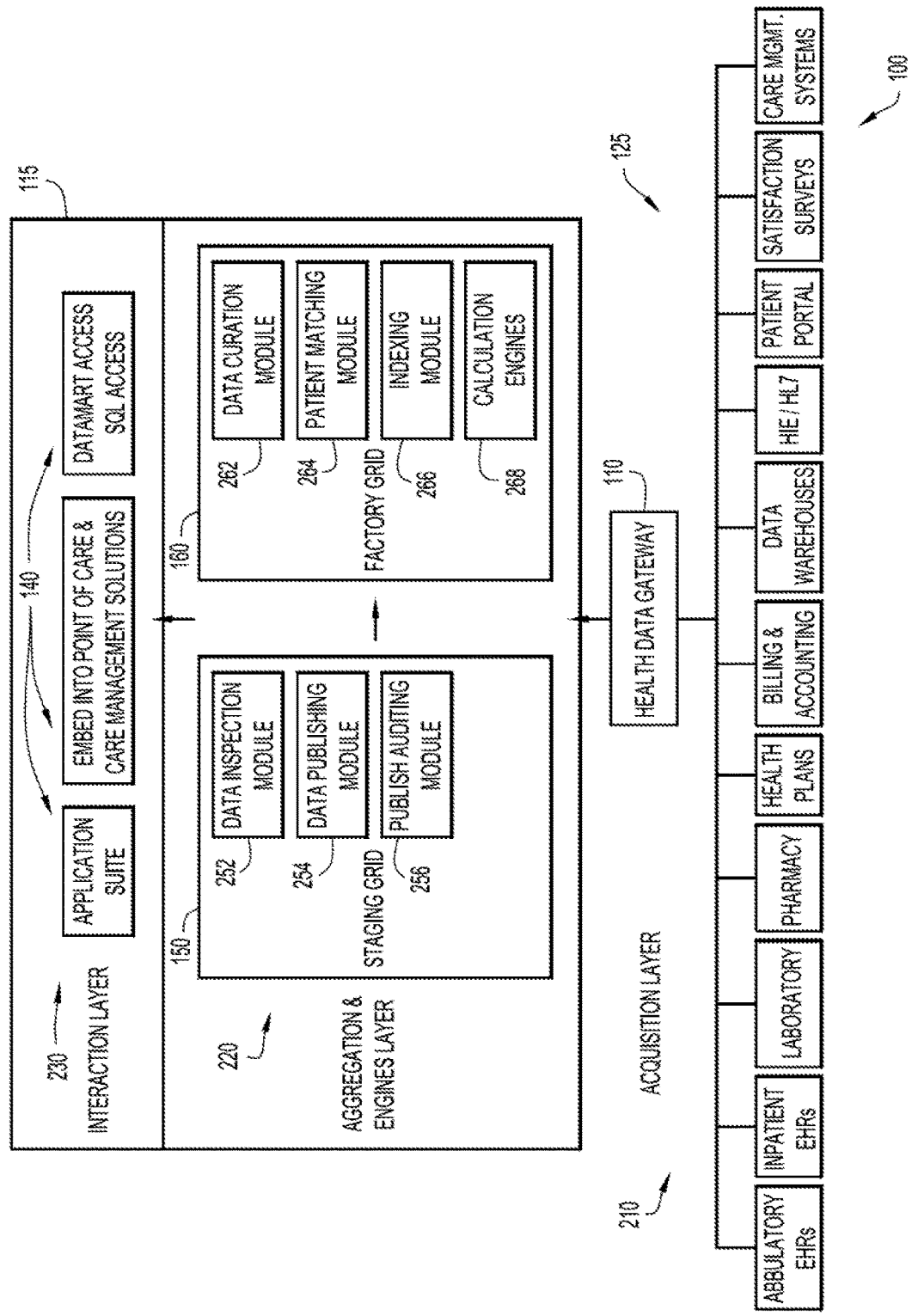
FIG. 2 is a diagrammatic illustration of the data center of the computing environment of FIG. 1 according to an embodiment of the present invention.

Referring to FIG. 2, health data gateway 110 of one or more healthcare networks is configured to acquire data from data sources 125 of those healthcare networks (e.g., ambulatory electronic health records (EHR), inpatient electronic health records (EHR), laboratory data, pharmacy data, health plan data, billing and accounting data, data warehouses, health information exchange (HIE)/HL7 data, patient portal, satisfaction surveys, care management systems, etc.) and transmit the acquired data to gateway controller 145 of data center 115 as described above. The healthcare networks and/or data sources 125 form an acquisition layer 210 providing data to data center 115 via health data gateway 110.

Gateway controller 145 receives the incoming data from communications network 120 and processes that data to staging grid 150 employing data models of the source systems. Staging grid 150 includes a data inspection module 252, a data publishing module 254, and a publish auditing module 256 to inspect, publish, and audit the data to factory grid 160 in accordance with the data model employed by the factory grid.

Figure 2A:
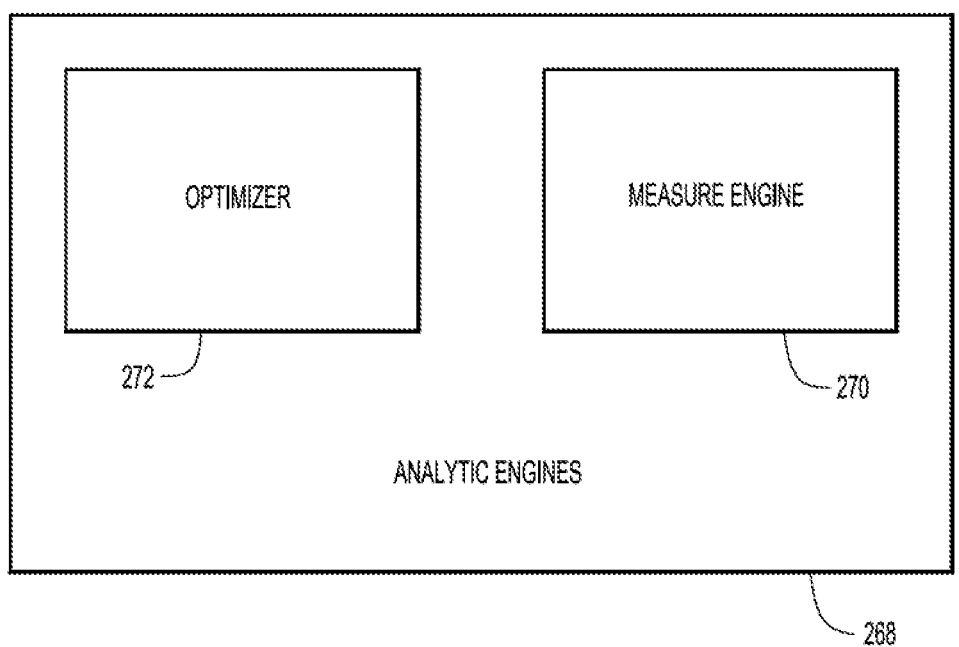
FIG. 2A is a diagrammatic illustration of analytic engines disposed within the factory grid of the data center of FIG. 2.

Factory grid 160 includes a data curation module 262, a patient matching module 264, an indexing module 266, and various calculation or analytic engines 268. Data curation module 262 performs data curation operations including mapping codes, data cleansing, and standardization, while patient matching module 264 performs patient matching operations to determine records associated with the same patient. Indexing module 266 performs indexing operations including combining records based on patient matching, mappings, and application of risk models. The analytic engines perform the desired analytics from an interaction layer 230 enabling application server cluster 140 to provide various applications for processing and accessing the data (e.g., analytic applications, SQL access, etc.). Referring to FIG. 2A, the analytic engines 268 include a measure engine 270 that determines measure specifications for patient populations and an optimizer 272 that translates the measure specifications into compressed specifications as described herein. The staging and factory grids form an aggregation and engines layer 220 to process the acquired data, while the queries are handled by factory grid 160 in conjunction with application server cluster 140 to produce desired results for the interaction layer.

The various applications of application server cluster 140 may be provided in a cloud environment. It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones or other devices, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly release to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

Figure 3:
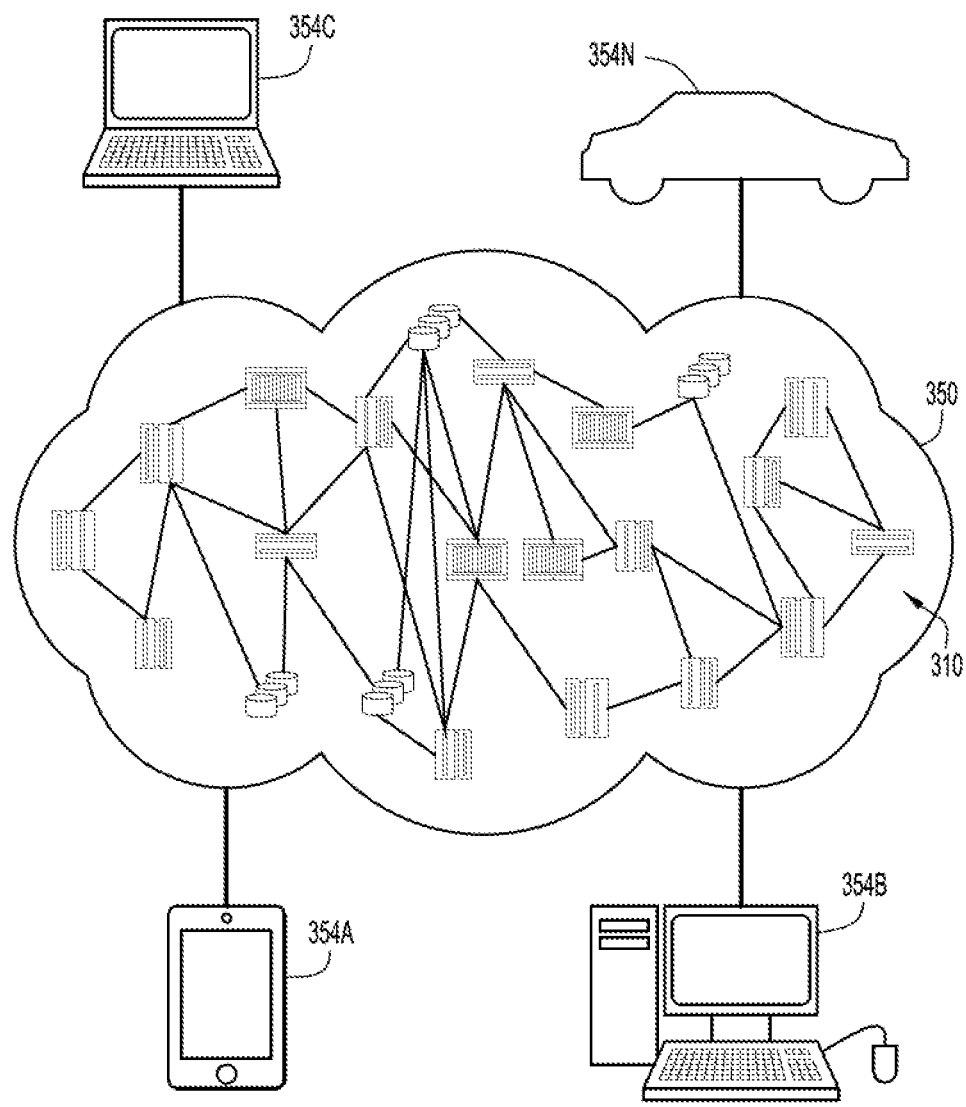
FIG. 3 is a diagrammatic illustration of an example cloud computing environment for the computing environment of FIG. 1 according to an embodiment of the present invention.

A cloud computing environment is service oriented with a focus on statelessness, low coupling, modularity, and semantic interoperability. At the heart of cloud computing is an infrastructure comprising a network of interconnected nodes. Referring now to FIG. 3, illustrative cloud computing environment 350 is depicted. As shown, cloud computing environment 350 comprises one or more cloud computing nodes 310 with which local computing devices used by cloud consumers, such as, for example, personal digital assistant (PDA) or cellular telephone 354A, desktop computer 354B, laptop computer 354C, and/or automobile computer system 354N may communicate. Nodes 310 may communicate with one another. They may be grouped (not shown) physically or virtually, in one or more networks, such as Private, Community, Public, or Hybrid clouds as described hereinabove, or a combination thereof. This allows cloud computing environment 350 to offer infrastructure, platforms and/or software as services for which a cloud consumer does not need to maintain resources on a local computing device. It is understood that the types of computing devices 354A-N shown in FIG. 3 are intended to be illustrative only and that computing nodes 310 and cloud computing environment 350 can communicate with any type of computerized device over any type of network and/or network addressable connection (e.g., using a web browser).

Figure 4:
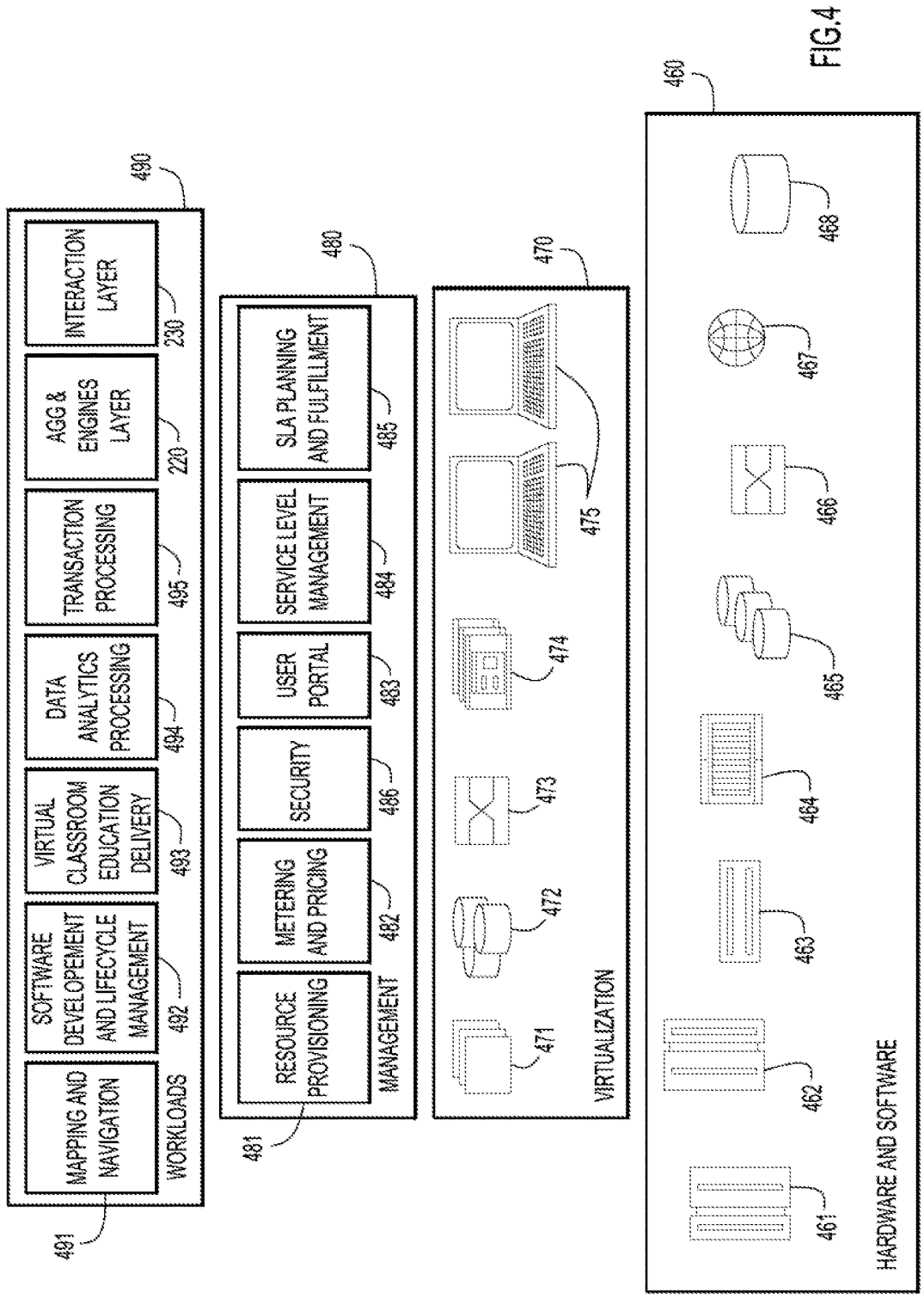
FIG. 4 is a diagrammatic illustration of abstraction model layers according to an embodiment of the present invention.

Referring now to FIG. 4, a set of functional abstraction layers provided by cloud computing environment 350 (FIG. 3) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 460 includes hardware and software components. Examples of hardware components include: mainframes 461; RISC (Reduced Instruction Set Computer) architecture based servers 462; servers 463; blade servers 464; storage devices 465; and networks and networking components 466. In some embodiments, software components include network application server software 467 and database software 468.

Virtualization layer 470 provides an abstraction layer from which the following examples of virtual entities may be provided: virtual servers 471; virtual storage 472; virtual networks 473, including virtual private networks; virtual applications and operating systems 474; and virtual clients 475.

In one example embodiment, management layer 480 may provide some or all of the functions for data center 115 described herein. Resource provisioning 481 provides dynamic procurement of computing resources and other resources that are utilized to perform tasks within the cloud computing environment. Metering and Pricing 482 provide cost tracking as resources are utilized within the cloud computing environment, and billing or invoicing for consumption of these resources. In one example, these resources may comprise application software licenses. Security 486 provides identity verification for cloud consumers and tasks, as well as protection for data and other resources. User portal 483 provides access to the cloud computing environment for consumers and system administrators. Service level management 484 provides cloud computing resource allocation and management such that required service levels are met. Service Level Agreement (SLA) planning and fulfillment 485 provide pre-arrangement for, and procurement of, cloud computing resources for which a future requirement is anticipated in accordance with an SLA.

Workloads layer 490 provides examples of functionality for which the cloud computing environment may be utilized. Examples of workloads and functions which may be provided from this layer include: mapping and navigation 491; software development and lifecycle management 492; virtual classroom education delivery 493; data analytics processing 494; transaction processing 495; aggregation and engines layer 220 (FIG. 2); and interaction layer 230 (FIG. 2).

Figure 5:
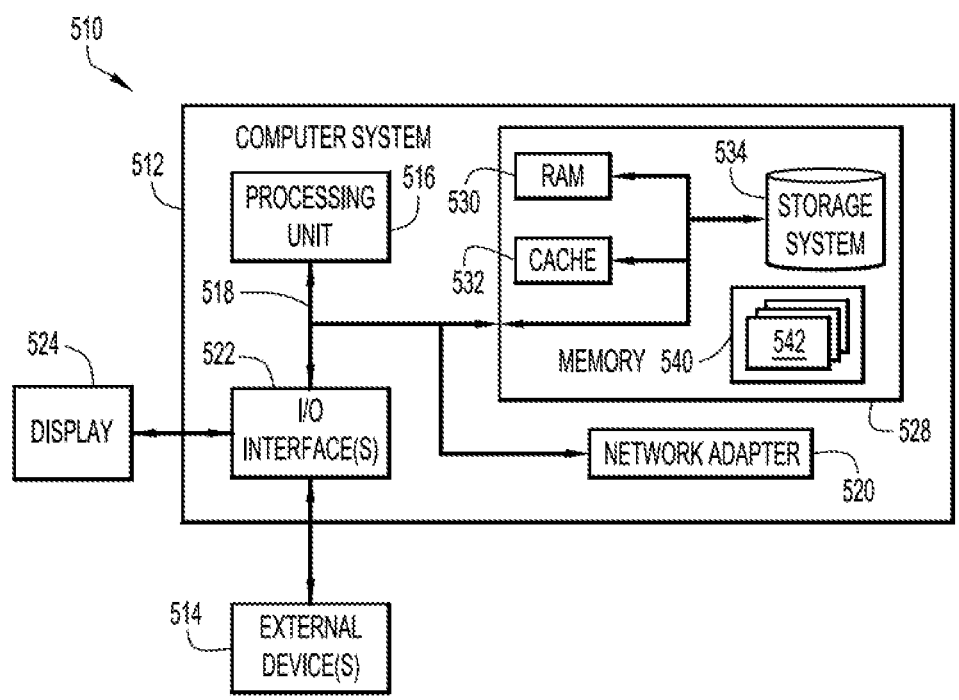
FIG. 5 is a block diagram of a computing node according to an embodiment of the present invention.

Referring now to FIG. 5, a schematic of an example of a computing node or device 510 of computer environment 100

(e.g., health data gateway 110, application server cluster 140, gateway controller 145, computing nodes of staging grid 150, computing nodes of factory grids 160, etc.) and cloud environment 350 (e.g., cloud computing node 310, etc.) is shown. The computing node or device is only one example of a suitable computing node for computing environment 100 and cloud computing environment 350 and is not intended to suggest any limitation as to the scope of use or functionality of embodiments of the invention described herein. Regardless, computing node 510 is capable of being implemented and/or performing any of the functionality set forth herein.

In computing node 510, there is a computer system 512 which is operational with numerous other general purpose or special purpose computing system environments or configurations. Examples of well-known computing systems, environments, and/or configurations that may be suitable for use with computer system 512 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 512 may be described in the general context of computer system executable instructions, such as program modules, being executed by a computer system. Generally, program modules may include routines, programs, objects, components, logic, data structures, and so on that perform particular tasks or implement particular abstract data types. Computer system 512 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, computer system 512 is shown in the form of a general-purpose computing device. The components of computer system 512 may include, but are not limited to, one or more processors or processing units 516, a system memory 528, and a bus 518 that couples various system components including system memory 528 to processor 516.

Bus 518 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 512 typically includes a variety of computer system readable media. Such media may be any available media that is accessible by computer system 512, and it includes both volatile and non-volatile media, removable and non-removable media.

System memory 528 can include computer system readable media in the form of volatile memory, such as random access memory (RAM) 530 and/or cache memory 532. Computer system 512 may further include other removable/non-removable, volatile/non-volatile computer system storage media. By way of example only, storage system 534 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 518 by one or more data media interfaces. As will be further depicted and described below, memory 528 may include at least one program product having a set (e.g., at least one) of program modules that are configured to carry out the functions of embodiments of the invention.

Program/utility 540, having a set (at least one) of program modules 542, may be stored in memory 528 by way of example, and not limitation, as well as an operating system, one or more application programs, other program modules, and program data. Each of the operating system, one or more application programs, other program modules, and program data or some combination thereof, may include an implementation of a networking environment. Program modules 542 generally carry out the functions and/or methodologies of embodiments of the invention as described herein.

Computer system 512 may also communicate with one or more external devices 514 such as a keyboard, a pointing device, a display 524, etc.; one or more devices that enable a user to interact with computer system 512; and/or any devices (e.g., network card, modem, etc.) that enable computer system 512 to communicate with one or more other computing devices. Such communication can occur via Input/Output (I/O) interfaces 522. Still yet, computer system 512 can communicate with one or more networks such as a local area network (LAN), a general wide area network (WAN), and/or a public network (e.g., the Internet) via network adapter 520. As depicted, network adapter 520 communicates with the other components of computer system 512 via bus 518. It should be understood that although not shown, other hardware and/or software components could be used in conjunction with computer system 512. Examples, include, but are not limited to: microcode, device drivers, redundant processing units, external disk drive arrays, RAID systems, tape drives, and data archival storage systems, etc.

Figure 6:
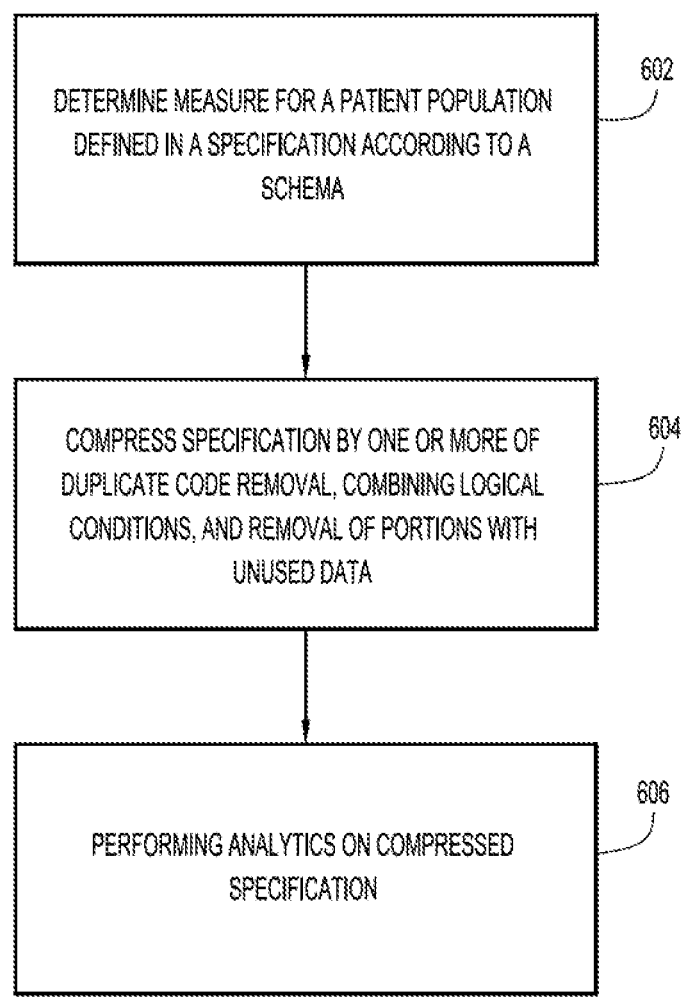
FIG. 6 is a procedural flowchart illustrating a manner of optimizing a measure specification according to an embodiment of the present invention.

A manner of optimizing performance of analytics in relation to data for the computing environment 100 of FIG. 1 is now described with reference to FIG. 6. As previously noted, the factory grid 160 includes analytic engines 268 to perform analytics of the patient data (e.g., based on queries received from end-user systems 118 and other end-user systems 155 accessing data center 115 over network 120). In performing analytics in accordance with embodiments of the present invention, one or more measures are determined (at 602) by the measure engine for a patient population. Each measure comprises a specification or specification defined in a suitable schema that is used by the data center 115 to perform the analytics. In an example embodiment, the measure specifications are defined in an XML (extensible markup language) schema, e.g., in an XML-type language specifically used within the data center in relation to analyzing data stored by data sources 125 (also referred to herein as an XML type Measure Definition Language or MDL).

An MDL specification specifies one or more criteria for the patient population. In an example embodiment, a measure is defined including a numerator and a denominator, where the numerator can define a specific or narrower class or group of patients while the denominator defines a broader class or group of patients (e.g., the broader group or class includes patients of the narrower group or class). For example, a measure may include a value for patients (as defined by patient health records) within the data sources of the health care network that are diabetic and also have a body mass index (BMI) above or below a certain threshold value and/or within a certain range of values. In this example, the numerator can be defined as the number of patients within the data sources meeting the criteria of being diabetic and having a BMI value within a specified range, while the denominator might be any larger group of patients within the data sources (e.g., total number of patients within the data sources, number of patients within the data sources being diabetic, etc.). A measure can further be defined as any one or more combinations of numerators and denominators and/or include any one or more different combinations of criteria for numerators and/or denominators. Measures can thus be defined to provide information of a ratio or percentage of certain types or groups of patients (e.g., patients associated with certain specific medical conditions) that are in relation to some larger group of patients based upon the defined numerator and defined denominator of the MDL specification. Alternatively, a measure may not include a numerator or denominator in its definition but instead define a class or group of patients in some other manner that is suitable for performing analytics on the patient data.

The MDL specification for a measure includes sections for the criteria defining the measure. For MDL specifications including numerators and denominators defining a class or group of patients, the MDL specification includes sections for the numerator and denominator delineated by tags (e.g., "<numerator>" and "<denominator>"). Each section of the MDL specification specifies the criteria or conditions for patients to be included within the respective numerator and denominator.

While the MDL specifications provided by the measure engine 272 are useful in performing data analytics based upon the defined measures, there can be certain inefficiencies associated with such MDL specifications.

For example, an MDL specification provided by the measure engine 270 can include codes that represent certain specific patient categories, groups or classes within the healthcare network. In particular, measure definitions can be generated using a variety of pre-defined medical ontologies, where a particular medical concept can be commonly defined using multiple codes from various ontologies. However, the analytic engines 268 may only utilize one ontology per concept when performing data analytics. Thus, certain codes within a generated MDL specification may be unused for a particular analytic operation.

Further, an MDL specification can include certain logical conditions, such as OR statements (e.g., OR statements associated with numerator and/or denominator sections of the MDL specification). The OR statements are provided as a group with a set of codes, where only a single code is true in order for a specified condition to be true. The group of OR statements is typically provided within an XML specification as separate lines for each code (i.e., one code per line). However, this configuration in the XML specification causes the analytic engines to create a new object for each code. If there are several (e.g., thousands or tens of thousands) of codes in the OR group, this results in a significantly large number of objects that are created by the analytic engines when only a single code that satisfies the specified OR condition need be analyzed.

Further still, due to human nature in defining documents, an MDL specification may include frequent occurrences of duplicate codes or duplicate blocks of codes. This can unnecessarily increase the size of the MDL specification and also result in the unnecessary creation of further objects to be processed by the analytics engines.

The optimizer 272 (at 604) analyzes the MDL specification provided by the measure engine 270 and compresses the MDL specification for optimized or more efficient processing by one or more analytic engines 268 downstream from the optimizer. In particular, the optimizer 272 receives as input from the measure engine 270 a measure definition in the form of an MDL specification and generates a compressed MDL specification that adheres to the same XML schema as the original MDL specification. The optimizer 272 can be configured to iteratively run various schema specific compression and optimization algorithms, including duplicate code removal, OR group optimization, and extraneous code removal.

For example, for each group of OR statements, which are formed vertically within the specification (with one code listed per line of the specification), the optimizer 272 condenses the OR group such that all sets of codes in the OR group are provided within a single line of the specification. This results in only one object being created by an analytic engine 268 processing the compressed MDL specification (i.e., a single object for the code that satisfied the OR condition).

The optimizer 272 further finds duplicate code statements and/or duplicate blocks of code statements and removes all duplicates from the MDL specification during compression/optimization processing of the MDL specification. The optimizer 272 also analyzes the MDL specification to determine whether any codes are extraneous or unnecessary within the MDL specification and removes statements including such codes during compression/optimization processing of the MDL specification. For example, an MDL specification can be generated that includes one or more lines or statements that include two or more codes. For a particular analytic operation, one type of code may take precedence over another type of code (e.g., one type of code for a criteria or condition may be unnecessary when another type of code is also provided for the same criteria or condition). The optimizer 272 (utilizing one or more algorithms) determines which code types are unnecessary for the analytic operation and removes such codes from the MDL specification during compression/optimization processing. This avoids unnecessary processing of the unneeded codes during processing of the compressed MDL specification by the analytic engine(s) 268 downstream of the optimizer 272.

The compressed MDL specification generated by the optimizer 272 is provided to one or more analytic engines 268 located downstream from the optimizer. The downstream analytic engine(s) 268 perform analytics on patient data within the data sources using the compressed MDL specification (at 606).

An example is now described of an MDL specification that is compressed in accordance with the invention embodiments as described herein. In the example, the MDL specification is for a patient measure that includes sections defining criteria for numerators and denominators. The original MDL specification provided by the measure engine 270 (prior to compression) is as follows:

```xml
<?xml version="1.0" encoding="UTF-8"?>
<mdl measureResultType="DENOMINATOR_VALUE">
<linkFilters>
    <filter name="OutpatientObsEDNonAcute">
        <encounterLink linkType="ENCOUNTER">
        <or>
            <procedure cptCodes="99201"/> <!-- CPT: 99201: Evaluation
    and management of new outpatient in office or other outpatient facility
    (procedure) -->
            <procedure cptCodes="99202"/> <!-- CPT: 99202: Evaluation
    and management of new outpatient in office or other outpatient facility
    (procedure) -->
            <procedure cptCodes="99203"/> <!-- CPT: 99203: Evaluation
    and management of new outpatient in office or other outpatient facility
    (procedure) -->
            <procedure cptCodes="99205"/> <!-- CPT: 99205: Evaluation
    and management of new outpatient in office or other outpatient facility
    (procedure) -->
            <procedure cptCodes="99211"/> <!-- CPT: 99211: Evaluation
    and management of established outpatient in office or other outpatient
    facility (procedure) -->
            <procedure cptCodes="99212"/> <!-- CPT: 99212: Evaluation
    and management of established outpatient in office or other outpatient
    facility (procedure) -->
        </or>
        </encounterLink>
    </filter>
</linkFilters>
<denominator>
    <cohort>
        <or>
        <diagnosis icdCodes="250" snomedIds="73211009" isPOA="true"/> <!--
ICD-9-CM: 250: Diabetes mellitus (disorder) -->
        <diagnosis icdCodes="250.0" snomedIds="73211009" /> <!-- ICD-9-CM:
250.0 : Diabetes mellitus (disorder) -->
        <diagnosis icdCodes="250.00" snomedIds="44054006" /> <!-- ICD-9-CM:
250.00 : Diabetes mellitus type 2 (disorder) -->
        <diagnosis icdCodes="250.01" snomedIds="46635009" isPOA="true"/> <!--
ICD-9-CM: 250.01 : Diabetes mellitus type 1 (disorder) -->
        <diagnosis icdCodes="250.02" snomedIds="443694000" /> <!-- ICD-9-CM:
250.02: Type II diabetes mellitus uncontrolled (finding) -->
        <diagnosis icdCodes="250.03" snomedIds="444073006" /> <!-- ICD-9-CM:
250.03 : Type I diabetes mellitus uncontrolled (finding) -->
        <diagnosis icdCodes="" snomedIds="444073006" /> <!-- ICD-9-CM: 250.03
: Type I diabetes mellitus uncontrolled (finding) -->
        </or>
        <or>
        <diagnosis icdCodes="250" snomedIds="73211009" isPOA="true"/> <!--
ICD-9-CM: 250: Diabetes mellitus (disorder) -->
        <diagnosis icdCodes="250.0" snomedIds="73211009" /> <!-- ICD-9-CM:
250.0 : Diabetes mellitus (disorder) -->
        <diagnosis icdCodes="250.00" snomedIds="44054006" /> <!-- ICD-9-CM:
250.00 : Diabetes mellitus type 2 (disorder) -->
        <diagnosis icdCodes="250.01" snomedIds="46635009" isPOA="true"/> <!--
ICD-9-CM: 250.01 : Diabetes mellitus type 1 (disorder) -->
        <diagnosis icdCodes="250.02" snomedIds="443694000" /> <!-- ICD-9-CM:
250.02: Type II diabetes mellitus uncontrolled (finding) -->
        <diagnosis icdCodes="250.03" snomedIds="444073006" /> <!-- ICD-9-CM:
250.03 : Type I diabetes mellitus uncontrolled (finding) -->
        <diagnosis icdCodes="" snomedIds="444073006" /> <!-- ICD-9-CM: 250.03
: Type I diabetes mellitus uncontrolled (finding) -->
        </or>
    </cohort>
</denominator>
<numerator>
    <cohort>
    </cohort>
</numerator>
<exclusion>
    <encounter type="INPATIENT">
    <or>
        <!-- CABG -->
        <procedure icdCodes="36.1" snomedIds="" /> <!-- ICD-9-CM: 36.1:
Bypass anastomosis for heart revascularization -->
        <procedure cptCodes="33510" snomedIds="232717009" /> <!-- CPT:
33510: Coronary artery bypass grafting (procedure) -->
        <procedure cptCodes="33511" snomedIds="232720001" /> <!-- CPT:
33511 : Coronary artery bypass grafts x 2 (procedure) -->
        <procedure cptCodes="33512" snomedIds="232721002" /> <!-- CPT:
33512: Coronary artery bypass grafts x 3 (procedure) -->
```

```
        <procedure cptCodes="33510" snomedIds="232722009" /> <!-- CPT:
    33513: Coronary artery bypass grafts x 4 (procedure) -->
      </or>
      </encounter>
  </exclusion>
</mdl>
```

In the example embodiment of the MDL specification, various ontology codes are pre-defined for patients associated with patient records stored within the data sources 125 of the healthcare network 105, where the MDL specification includes groups of OR statements in each of the numerator and denominator sections (identified by the <numerator> and <denominator> tags within the MDL specification). In the example embodiment, medical ontology codes represent The resulting compressed MDL from the optimizer after performance of duplicate removal, "OR" group optimization, and extraneous code removal (e.g., removal of "snomedIDS" codes in statements or lines of the MDL specification that include both "snomedIDS" and "icdCodes" codes) is as follows:

```
<?xml version="1.0" encoding="UTF-8" standalone="yes"?>
<mdl measureResultType="DENOMINATOR_VALUE">
<linkFilters>
    <filter name="OutpatientObsEDNonAcute">
    <encounterLink linkType="ENCOUNTER">
      <or>
        <procedure cptCodes="99211|99212|99201|99202|99203|99205"/>
      </or>
    </encounterLink>
    </filter>
</linkFilters>
<denominator>
    <cohort>
    <or>
        <diagnosis icdCodes="250.01|250" isPOA="true"/>
        <diagnosis snomedIds="444073006"/>
        <diagnosis icdCodes="250.02|250.0|250.03|250.00"/>
    </or>
    </cohort>
</denominator>
<numerator>
    <cohort/>
</numerator>
<exclusion>
    <encounter type="INPATIENT">
    <or>
        <procedure icdCodes="36.1"/>
        <procedure cptCodes="33512|33510|33511"/>
    </or>
    </encounter>
</exclusion>
</mdl>
``` medical health diseases and/or other health issues associated with patient records such as different types of diabetes and different types of heart related issues. However, any other types of medical ontology codes may also be utilized within the MDL specification based upon patient information desired to be obtained from the data sources by the analytic engines.

The optimizer 272 compresses and optimizes the MDL specification by removal of duplicate statements, optimizing groups of OR statements (condensing from various lines of codes in the group of OR statements into a single line of codes), and removal of extraneous or unused data portions. In particular, unused data portions can exist in statements or lines of the MDL specification that include both "icdCodes" codes (patient diagnosis codes of a first type) and "snomedIds" codes (patient codes of a second type), where the "snomedIds" codes are not used when both types of codes are present in a particular statement or line of the MDL specification. The optimizer 272 removes the extraneous codes from the statements to condense the MDL specification.

It is evident from a comparison of the original (uncompressed) MDL specification and the compressed MDL specification that the codes for OR statement groups in different sections are compressed from multiple lines to a single line (e.g., various cptCodes in the <linkFilters> section are compressed from multiple lines to the following single line: <procedure cptCodes="99211|99212|99201|99202|99203|99205"/>). It is further evident that lines of the original MDL specification that include both "snomedIDS" and "icdCodes" codes are revised in the compressed MDL specification to include only "icdCodes" codes (i.e., extraneous or unneeded data for a particular analytic to be performed is removed from the MDL specification). In addition, certain duplicate lines of the original MDL specification have also been removed from the compressed MDL specification.

The compressed MDL specification has a reduced or lesser (i.e., smaller) memory size in relation to the original (uncompressed) MDL specification and is further optimized by moving the vertical grouping of OR statements into a single (horizontal) line (which in turn results in downstream analytic processing creating a single object for the OR condition instead of multiple objects as would be the case with the original, uncompressed MDL specification). This results in more efficient processing of the data analytic operations to obtain patient information based upon end user queries.

The previous embodiment describing both an original MDL specification and a compressed MDL specification has been provided for example purposes as a representation of how the invention embodiments operate to achieve compression and optimization of the MDL specification. In many instances the number of grouped OR statements can be significantly large (e.g., hundreds, thousands or even more lines of codes associated with an OR group), along with a significant number of duplicate lines and/or extraneous code, where a compressed MDL specification can significantly reduce the number of statements or lines and overall memory size in comparison to the original (uncompressed) MDL specification. The compression and optimization of the MDL specification provides a significant effect in optimizing processing of data analytics associated with the MDL specification, which in turn enhances the speed and efficiency of performance of the system in response to patient data queries by end users.

It will be appreciated that the embodiments described above and illustrated in the drawings represent only some of the many ways of implementing embodiments for compression and optimization of a specification utilizing a schema to perform analytics on data sources.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, etc.). These systems may include any types of monitors and input devices (e.g., keyboard, mouse, voice recognition, etc.) to enter and/or view information.

It is to be understood that the software (e.g., modules for the measure engine, optimizer, other analytic engines, etc.) of the present invention embodiments may be implemented in any desired computer language and could be developed by one of ordinary skill in the computer arts based on the functional descriptions contained in the specification and flow chart illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow chart may be modified in any manner that accomplishes the functions described herein. In addition, the functions in the flow chart or description may be performed in any order that accomplishes a desired operation.

The software of the present invention embodiments (e.g., software associated with the measure engine, optimizer, other analytic engines, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., algorithms associated with defining measure definitions, forming MDL specifications, compressing and optimizing specifications, etc.). The database system may be implemented by any number of any conventional or other databases, data stores or storage structures (e.g., files, databases, data structures, data or other repositories, etc.) to store information. The database system may be included within or coupled to the server and/or client systems. The database systems and/or storage structures may be remote from or local to the computer or other processing systems, and may store any desired data.

The present invention embodiments may utilize data in any desired structure (e.g., records, data objects, data structures, etc.), and associate the data with any desired entity (e.g., person, corporate or other business entity, healthcare or other medical related entity, healthcare provider, etc.).

The measure engine may form a specification that defines the constructs including criteria and/or conditions defining patient measures utilizing any suitable language or schema that may be implemented to perform analytics on data stored in data sources.

The optimizer can utilize any suitable algorithms to analyze a specification that defines a patient measure and includes criteria and/or conditions according to a schema and further compresses and optimizes the specification while adhering to the same schema. The analytic engines can further utilize any suitable algorithms to perform analytics on data utilizing the compressed specification.

The present invention embodiments may employ any number of any type of user interface (e.g., Graphical User Interface (GUI), command-line, prompt, etc.) for obtaining or providing information (e.g., queries, providing patient measures, analytic results, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The present invention embodiments are not limited to the specific tasks or algorithms described above, but may be utilized for associating data from various data systems with any type of common entity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment and terminology was chosen and described in order to best explain the principles of the invention and the practical application, and to enable others of ordinary skill in the art to understand the invention for various embodiments with various modifications as are suited to the particular use contemplated.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method of optimizing performance of analytics comprising:
analyzing, by at least one processor, a specification of an analytic produced in accordance with a schema, wherein the specification indicates a set of conditions for members of a population to determine the analytic;
compressing, by the at least one processor, the specification by modifying constructs within the specification to produce a compressed specification of a reduced size and complying with the schema, wherein modifying the constructs within the specification includes removing duplicate portions, combining logical conditions, and removing portions with unused data; and
performing, by the at least one processor, the analytic based on the compressed specification.

2. The method of claim 1, wherein combining the logical conditions comprises:
consolidating a plurality of logical OR conditions into a common logical expression.

3. The method of claim 1, wherein the schema includes an XML schema.

4. The method of claim 1, wherein the specification includes statements including one or more types of codes that represent different ontologies of members within the population.

5. The method of claim 4, wherein the specification includes a first type of code and a second type of code, and the removing portions with unused data comprises removing the first type of code or the second type of code from the specification.

6. The method of claim 1, wherein the specification defines a measure of a patient population within a health care network, and the performing the analytic comprises performing the analytic for patient records stored within a plurality of data sources.

7. The method of claim 6, wherein the specification further defines a numerator including one or more sets of medical ontologies associated with the patient population and a denominator including another one or more sets of medical ontologies associated with the patient population, and the performing the analytic comprises determining a value associated with the patient records and based upon a ratio defined by the defined numerator and the defined denominator.

8. A system for optimizing performance of analytics comprising:
at least one hardware processor configured to:
analyze a specification of an analytic produced in accordance with a schema, wherein the specification indicates a set of conditions for members of a population to determine the analytic;
compress the specification by modifying constructs within the specification to produce a compressed specification of a reduced size and complying with the schema, wherein modifying the constructs within the specification includes removing duplicate portions, combining logical conditions, and removing portions with unused data; and
perform the analytic based on the compressed specification.

9. The system of claim 8, wherein the at least one hardware processor is configured to combine the logical conditions by:
consolidating a plurality of logical OR conditions into a common logical expression.

10. The system of claim 8, wherein the schema includes an XML schema.

11. The system of claim 8, wherein the specification includes statements including one or more types of codes that represent different ontologies of members within the population.

12. The system of claim 11, wherein the specification includes a first type of code and a second type of code, and the at least one hardware processor is configured to remove portions with unused data by removing the first type of code or the second type of code from the specification.

13. The system of claim 8, wherein the specification defines a measure of a patient population within a health care network, and the at least one hardware processor is configured to perform the analytic for patient records stored within a plurality of data sources.

14. The system of claim 13, wherein the specification further defines a numerator including one or more sets of medical ontologies associated with the patient population and a denominator including another one or more sets of medical ontologies associated with the patient population, and the at least one hardware processor is configured to perform the analytic by determining a value associated with the patient records and based upon a ratio defined by the defined numerator and the defined denominator.

15. A computer program product for optimizing performance of analytics, the computer program product comprising a computer readable storage device having program instructions embodied therewith, the program instructions executable by at least one processor to cause the at least one processor to:

analyze a specification of an analytic produced in accordance with a schema, wherein the specification indicates a set of conditions for members of a population to determine the analytic;

compress the specification by modifying constructs within the specification to produce a compressed specification of a reduced size and complying with the schema, wherein modifying the constructs within the specification includes removing duplicate portions, combining logical conditions, and removing portions with unused data; and perform the analytic based on the compressed specification.

16. The computer program product of claim 15, wherein the at least one processor is further caused to combine the logical conditions by consolidating a plurality of logical OR conditions into a common logical expression.

17. The computer program product of claim 15, wherein the schema includes an XML schema.

18. The computer program product of claim 15, wherein the specification includes statements including one or more types of codes that represent different ontologies of members within the population.

19. The computer program product of claim 18, wherein the specification includes a first type of code and a second type of code, and the at least one processor is further caused to remove portions with unused data by removing the first type of code or the second type of code from the specification.

20. The computer program product of claim 15, wherein the specification defines a measure of a patient population within a health care network, the measure comprising a numerator including one or more sets of medical ontologies associated with the patient population and a denominator including another one or more sets of medical ontologies associated with the patient population, and the at least one processor is further caused to perform the analytic by determining a value associated with patient records stored within a plurality of data sources, the value being determined based upon a ratio defined by the defined numerator and the defined denominator.

\* \* \* \* \*